US010725136B2

(12) United States Patent
Kerins et al.

(10) Patent No.: US 10,725,136 B2
(45) Date of Patent: *Jul. 28, 2020

(54) CEREBROSPINAL DIFFUSION PHANTOM

(71) Applicant: SYNAPTIVE MEDICAL (BARBADOS) INC., Bridgetown (BB)

(72) Inventors: Fergal Kerins, Ontario (CA); Timotheus Anton Gmeiner, Ontario (CA); Jeff Alan Stainsby, Ontario (CA); Chad Tyler Harris, Ontario (CA); Sheryl Rae Thingvold, Ontairo (CA); Gregory Allan Whitton, Ontario (CA)

(73) Assignee: Synaptive Medical (Barbados) Inc., Bridgetown (BB)

( * ) Notice: Subject to any disclaimer, the term of this patent is extended or adjusted under 35 U.S.C. 154(b) by 173 days.

This patent is subject to a terminal disclaimer.

(21) Appl. No.: 15/850,338

(22) Filed: Dec. 21, 2017

(65) Prior Publication Data

US 2018/0113186 A1 Apr. 26, 2018

Related U.S. Application Data

(63) Continuation of application No. 15/102,448, filed as application No. PCT/CA2015/050849 on Sep. 4, 2015, now Pat. No. 9,880,251.

(51) Int. Cl.
| | |
|---|---|
| *G01R 33/58* | (2006.01) |
| *G09B 23/30* | (2006.01) |
| *G01R 33/48* | (2006.01) |
| *G01R 33/563* | (2006.01) |
| *A61B 5/055* | (2006.01) |

(52) U.S. Cl.
CPC ......... *G01R 33/58* (2013.01); *G01R 33/4806* (2013.01); *G01R 33/56341* (2013.01); *G09B 23/30* (2013.01); *A61B 5/055* (2013.01)

(58) Field of Classification Search
CPC ............... G01R 33/58; G01R 33/4806; G01R 33/56341; G09B 23/30
See application file for complete search history.

(56) References Cited

U.S. PATENT DOCUMENTS

| | | | |
|---|---|---|---|
| 9,880,251 B2 * | 1/2018 | Kerins | G01R 33/4806 |
| 2017/0192076 A1 * | 7/2017 | Kerins | G01R 33/4806 |

* cited by examiner

*Primary Examiner* — Dixomara Vargas

(57) ABSTRACT

A cerebrospinal diffusion phantom including a housing having a shape and size configured for insertion into a magnetic resonance coil in one or more preselected poses. A scaffold support structure is mounted on an interior of said housing and a plurality of elongated diffusion mimicking members supported on the support array. The elongated diffusion mimicking members are affixed to the scaffold support structure such that elongated diffusion mimicking members extend in directions needed to substantially emulate a 3 dimensional arrangement of cerebrospinal diffusion fiber tracts in a living organism; modules for elimination of resolution based-bias, angular accuracy evaluation, diffusion rate calibration, and quality assurance image referencing. Each elongated diffusion mimicking member includes an aqueous component which can undergo diffusion along the elongated diffusion mimicking member. The phantom includes a cerebrospinal tissue mimic matrix material contained in the housing enveloping the array of elongated diffusion mimicking members.

20 Claims, 19 Drawing Sheets

CEREBROSPINAL DIFFUSION PHANTOM

FIELD

The present disclosure relates to medical phantom configured to be used for baseline calibration of MRI devices.

BACKGROUND

In the field of medicine phantoms or simulators have significant utility. Phantoms allow for the evaluation, analysis, and performance optimization of various imaging devices including magnetic resonance imaging (MRI) devices. They are more readily available and provide better consistency than use of a living specimen or cadaver.

In some biological tissues the diffusion of water is dependent on its interactions with the surrounding environment. Macromolecular structures, fibers, membranes and the dimension of the volumes containing the diffusing water reveal different information regarding the tissue in which the diffusion occurs. This information may provide insight into the architecture of anatomical and sub-anatomical structures; for example axonal fibers in the central nervous system.

Diffusion tensor imaging (DTI) is an MRI based imaging method that measures the anisotropic rate of water diffusion. The high degree of organization of white matter in the brain leads water to diffuse more rapidly in directions along white matter tracts because physical barriers such as mylinated axonal walls restrict water movement in other directions.

This unique ability of DTI to closely examine the fine structural changes of biological tissue by measuring anisotropic diffusion of water is very useful in determining the fine structure of white matter, delineating the boundaries of necrotic or damaged tissue, detection and confirmation of neurodegenerative diseases and brain disorders not found out by general medical imagining. The importance of DTI is underscored by the fact that it is the only way of studying white matter structure in vivo. This is a key element in being able to understand how these connections in the brain are affected during the progression of various diseases, and how cognitive and behavioral systems are linked to these changes.

The ability of DTI to describe connectivity in the brain has been clinically relevant for the study of neurological disorders as it can reveal abnormalities in white matter fiber structure and provide models of brain functionality.

This connectivity relies on the fact that functioning white matter consists of multiple axons contained within myelin sheaths with multiple axons arranged collinearly to form fascicles or bundles of nerve cells. The extra-cellular water contained in the spaces between myelin sheaths experiences anisotropic (directionally dependent) diffusion along the direction of the fascicle as the space is heavily restricted in perpendicular directions.

Presently, MR diffusion protocols may be used to measure both the rate and anisotropic property of diffusion. Differences in the rate of diffusion are associated with differences in cellular density which may vary between adjacent sub-anatomical structures—for example between ventricles and white matter, or, between healthy and some diseased tissues. For example cystic tumours would be characterized by regions of low (hypo-) cellularity and dense tumours such as a fibrous metastatic tumour would be characterized by high (hyper-) cellularity. The directionality (anisotropy) of diffusion is associated with tissue organization. Greater diffusional anisotropy indicates a more strongly directed diffusion, or highly structured tissue, such as white matter fiber bundles.

The practical applicability of DTI is limited by variation in the diffusion indices in different MR scanners; its inability to resolve multiple fiber populations; as well as by variations caused by the use of different imaging parameters (e.g. those used in longitudinal or multicenter trials). Therefore, the development of a standard DTI phantom to serve as a baseline for calibrated measurement and validated imaging would find utility.

Presently diffusion phantoms typically focus on either mimicking the rate or anisotropic nature of diffusion but not both simultaneously.

SUMMARY

The present disclosure describes an apparatus, approach, and methodology to produce cerebrospinal diffusion phantoms. The phantoms include a housing having a shape and size configured for insertion into a magnetic resonance coil in one or more preselected poses. A modular scaffold support structure is mounted on an interior of the housing and a plurality of elongated diffusion mimicking members supported on the modular support array. The elongated diffusion mimicking members are affixed to the adjustable scaffold support structure such that elongated diffusion mimicking members extend in directions needed to substantially emulate a 3 dimensional arrangement representative of cerebrospinal diffusion fiber tracts in a living organism. Each elongated diffusion mimicking member contains an aqueous component which can undergo diffusion along the elongated diffusion mimicking member. The phantom includes a cerebrospinal tissue mimic matrix material contained in the housing enveloping the array of elongated diffusion mimicking members. The housing is made of a material whose magnetic susceptibility reasonably matches that of the cerebrospinal mimic matrix material.

The phantom may include a module that enables the tuning of partial voxel volumes to decrease resolution based biases in DTI imaging. DTI imaging may be successfully applied for the quantification of fiber integrity and nerve fiber bundles consisting of a single fiber tract. To resolve fiber crossings, more elaborate diffusion imaging techniques like Q-Ball Imaging (QBI) may be used.

The phantom may include a module that enables the resolution of fiber crossings for evaluation of angular accuracy. In order to make accurate measurements of the relative difference between anisotropic and isotropic conditions within in vivo scans, operators need baseline or 'ground-truth' value for both of these diffusion states relative to one another. The phantom includes a module to enable such isotropic diffusion signal measurement.

In an embodiment there is disclosed a method for generating biomimetic micro-lumen structure containing bundles of flexible micro-rods from multi-material elements, comprising:

providing a spool of bicomponent micro fiber strand comprised of micro-rods of polypropylene embedded in a matrix of polyvinyl alcohol, unwinding the bicomponent micro fiber strand from said spool and winding it onto a generally square shaped spindle to generate a rod bundle with a set number of aligned bicomponent micro fiber strands, and said rod bundle having opposed ends;

immersing the rod bundle in water to dissolve the matrix of polyvinyl alcohol and thereafter placing the rod bundle in an ultrasonication bath, and repeating until all the polyvinyl alcohol has been removed and water is entrapped between adjacent micro-rods of polypropylene;

applying tension to the rod bundle by pulling the opposed ends of said rod bundle in opposite directions to align the micro-rods with each other in the bundle; and fastening said rod bundle on an interior of a cerebrospinal phantom to mimic diffusion tracts in cerebrospinal tissue.

A further understanding of the functional and advantageous aspects of the invention can be realized by reference to the following detailed description and drawings.

BRIEF DESCRIPTION OF THE DRAWINGS

Embodiments disclosed herein will be more fully understood from the following detailed description thereof taken in connection with the accompanying drawings, which form a part of this application, and in which.

DETAILED DESCRIPTION

Figure 1:
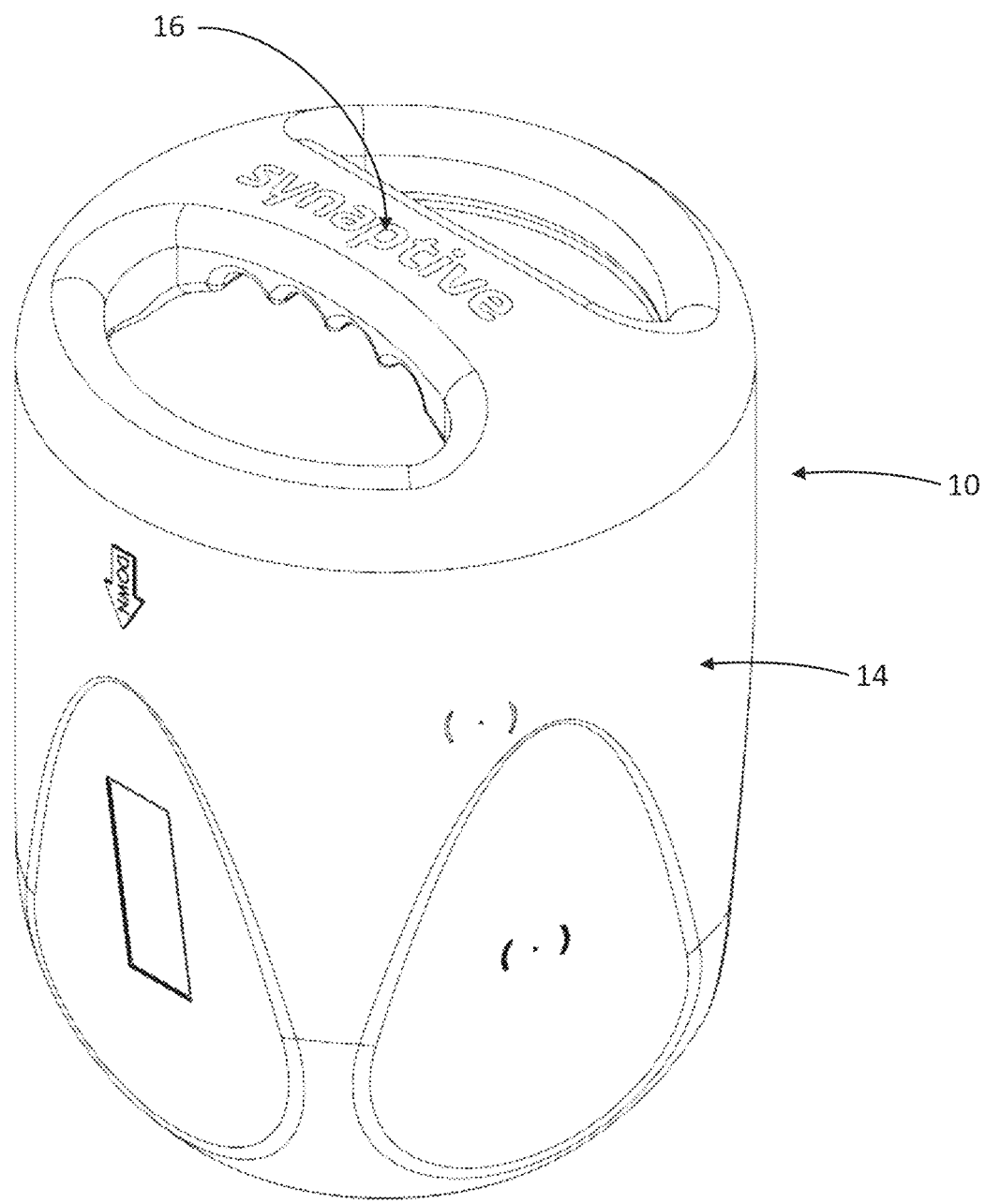
FIG. 1 is perspective view of an embodiment of a cerebrospinal diffusion phantom.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions.

The present specification discloses numerous example embodiments. The scope of the present patent application is not limited to the disclosed embodiments, but also encompasses combinations of the disclosed embodiments, as well as modifications to the disclosed embodiments.

References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Furthermore, it should be understood that spatial descriptions (e.g., "above," "below," "up," "left," "right," "down," "top," "bottom," "vertical," "horizontal," etc.) used herein are for purposes of illustration only, and that practical implementations of the structures described herein can be spatially arranged in any orientation or manner.

Numerous exemplary embodiments are described as follows. It is noted that any section/subsection headings provided herein are not intended to be limiting. Embodiments are described throughout this document, and any type of embodiment may be included under any section/subsection. Furthermore, disclosed embodiments may be combined with each other in any manner.

As used herein, the term "patient" is not limited to human patients and may mean any organism to be treated using the diffusion phantoms disclosed herein.

As used herein, "hydrogels" refer to materials that are formed by crosslinking polymer chains, through physical, ionic or covalent interactions and are known for their ability to absorb water. An example of a physical interaction that can give rise to a hydrogel is by thermal treatment of the liquid hydrogel precursor which, prior to being subjected to a freeze thaw cycle is a liquid or near liquid. The process of freezing the liquid precursor acts to freeze the water contained in the polymer/water mixture and ice particles causes the polymer strands to be topologically restricted in molecular motion by other chains thus giving rise to the "entanglement' cross linking to produce the hydrogel. Hydrogels that have been produced by a freeze thaw cycle are sometimes referred to as "cryogels".

Hydrogels characterized by cross linking that are produced through ionic or covalent interactions typically require a cross linking (XL) agent and/or an initiator and activation by methods such as heat or radiation.

Description of Inner and Outer Housings

Referring to FIGS. 1, 2, 3, 4 and 5, a cerebrospinal diffusion phantom constructed in accordance with the present invention is shown generally at 10. Diffusion phantom 10 comprises a base section 12, an exterior housing 14 adapted to couple with base section 12, and a handle 16 located in housing 14 adapted to be gripped by a user moving the phantom 10 around.

Figure 2:
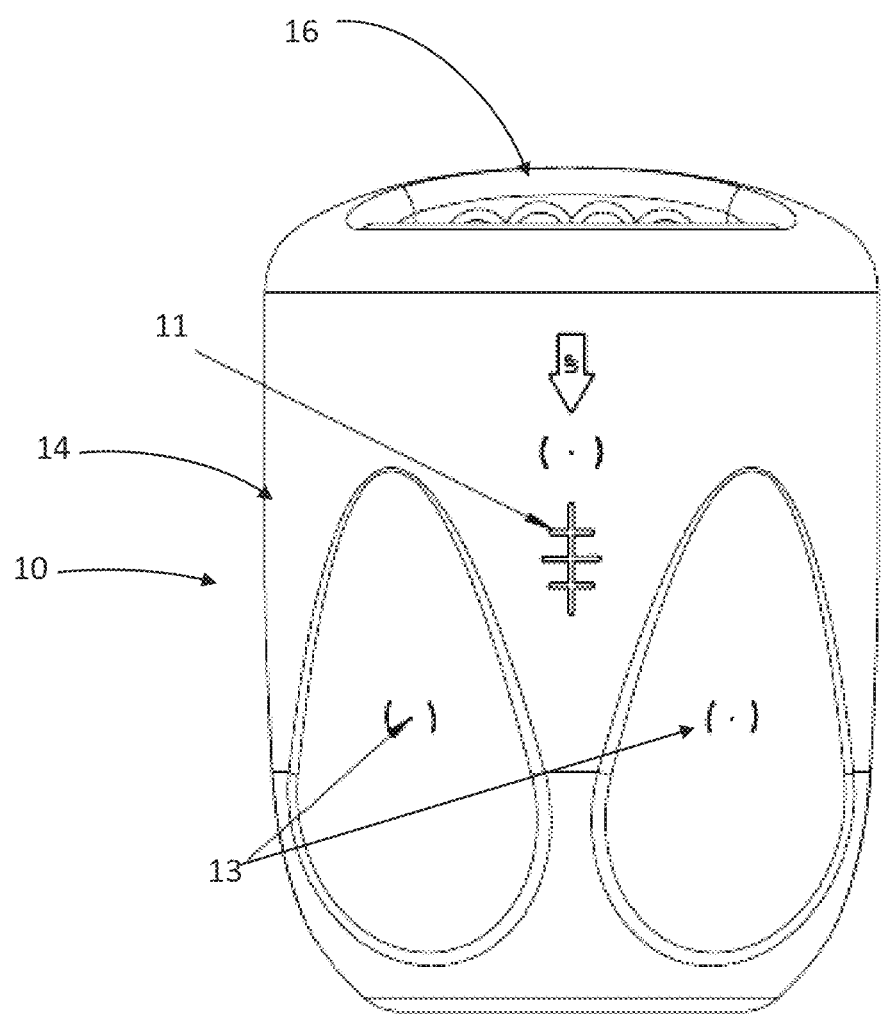
FIG. 2 is an elevation view of the diffusion phantom of FIG. 1.
Figure 3:
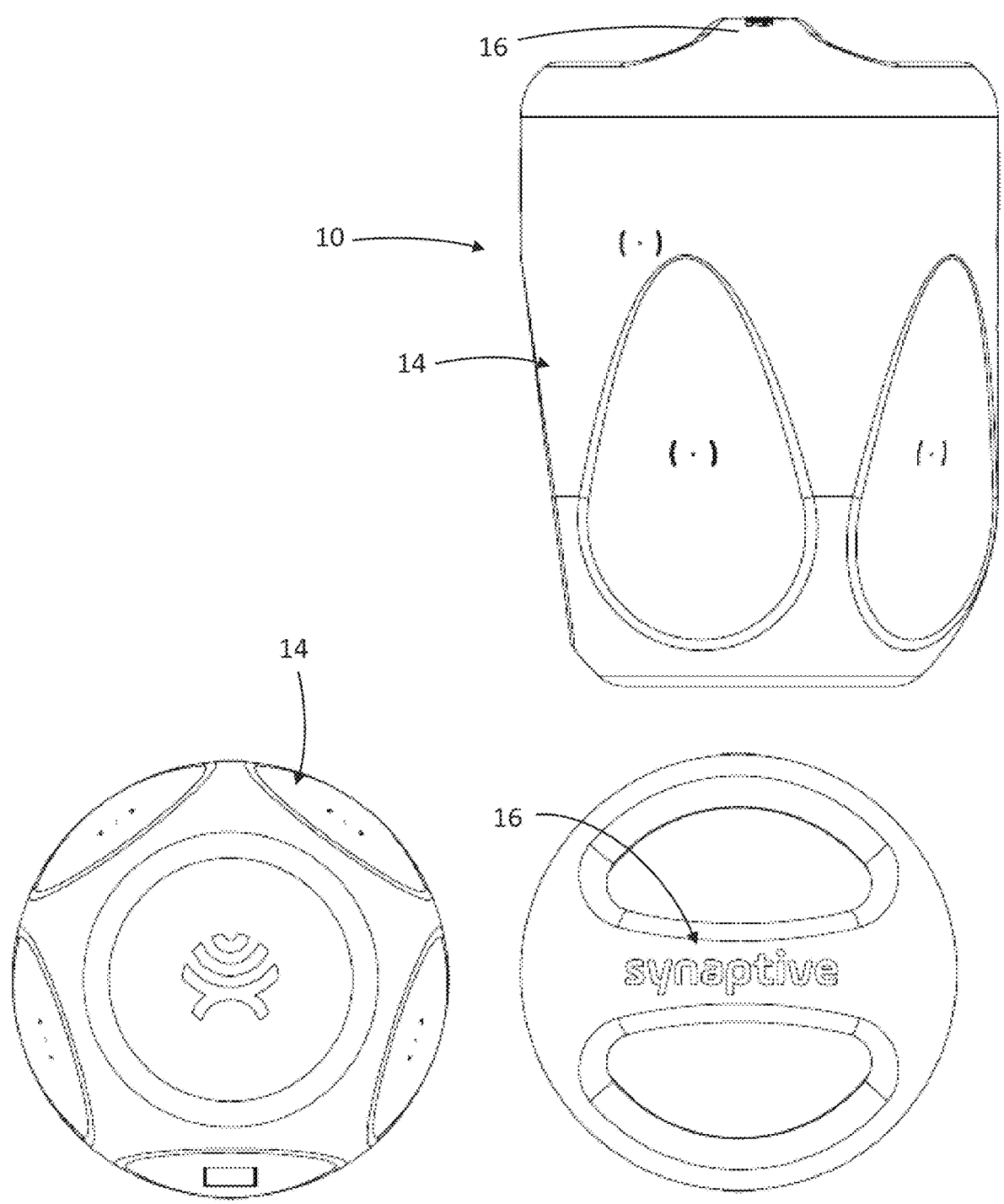
FIG. 3 is an elevation view of the diffusion phantom similar to FIG. 2 but rotated 90 degrees.

FIG. 2 also shows a scanning location reference marker 11 which provides a reference for locating the phantom 10 in a MRI machine. Phantom 10 in FIG. 2 also provides registration targets 13 where a navigation pointer tool can select these registration targets 13 to register phantom 10 with a medical navigation system can be mounted.

Figure 5:
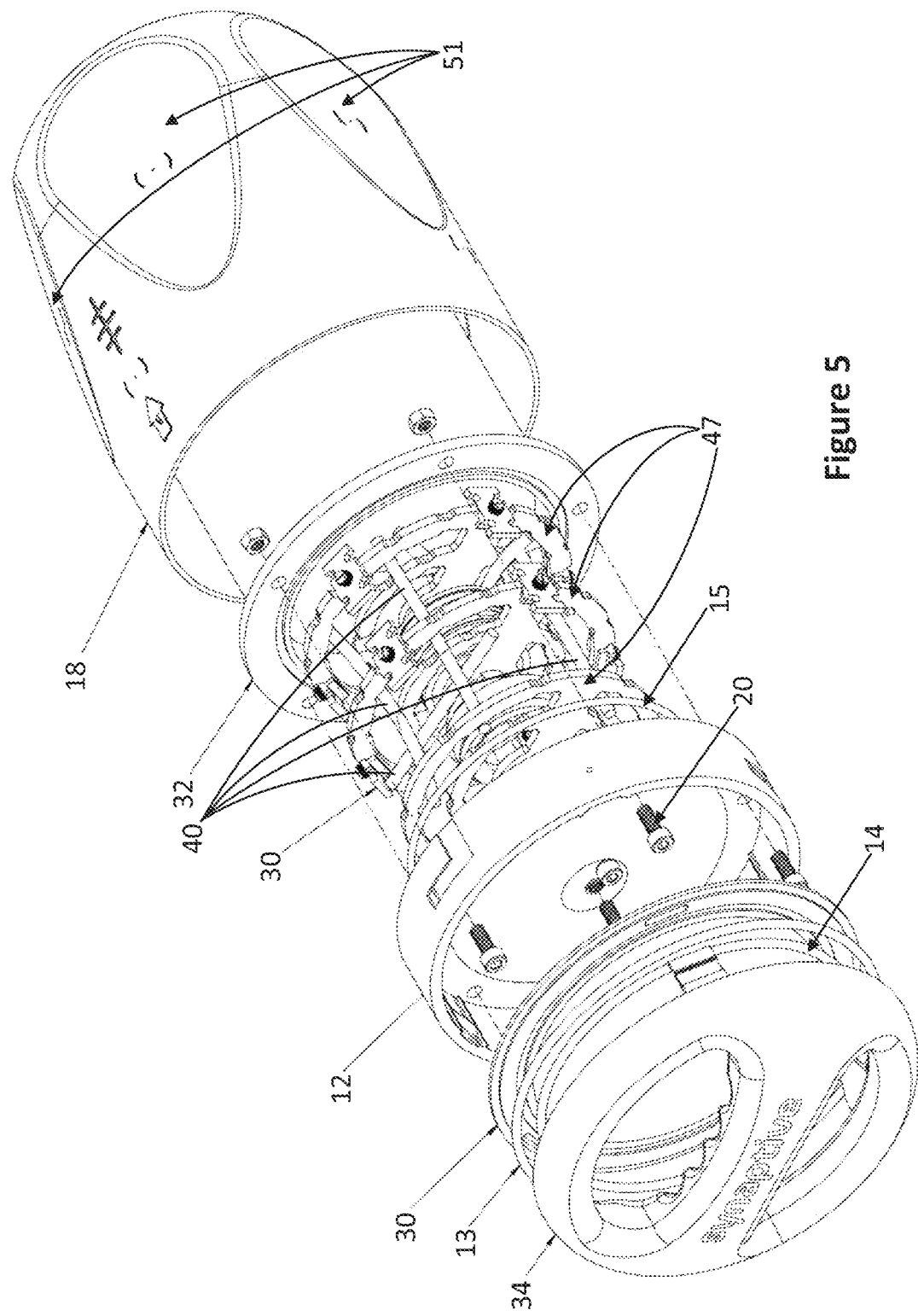
FIG. 5 is an exploded view of the phantom shown in FIGS. 1 to 4.
Figure 6:
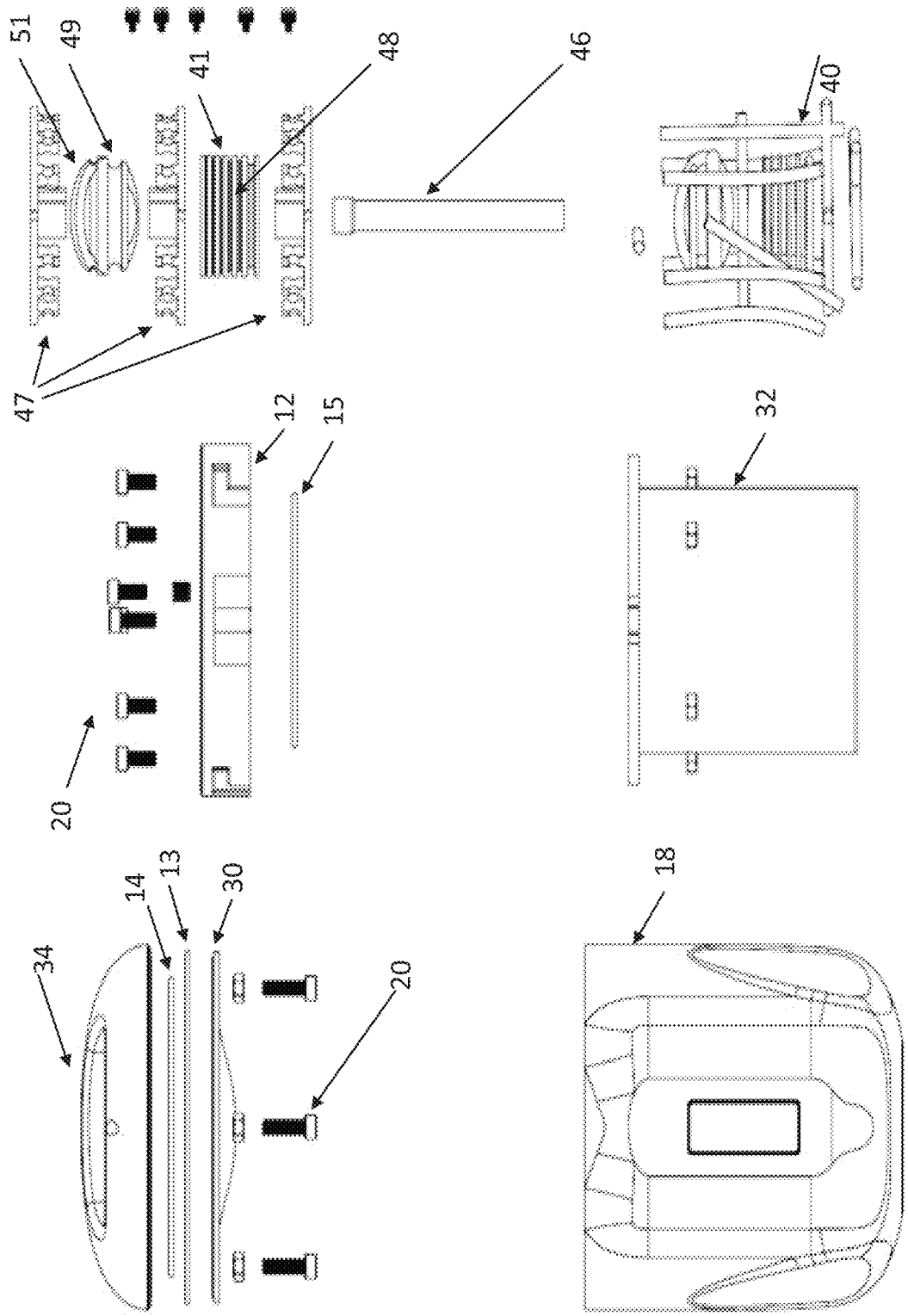
FIG. 6 is an extended exploded view of all components of the phantom of FIGS. 1 to 4.

FIGS. 5 and 6 shows an exploded view of phantom 10 in which it can be seen that base section 12 mounts to a seal plate 30, inner housing 32, and outer shell 18. When the phantom 10 is assembled, as can be seen from FIG. 5 one (1) o-ring 15 seals the inner housing 32 and the two (2) o-rings 13 and 14 seal the outer housing 18 and inner housing 32.

Figure 4:
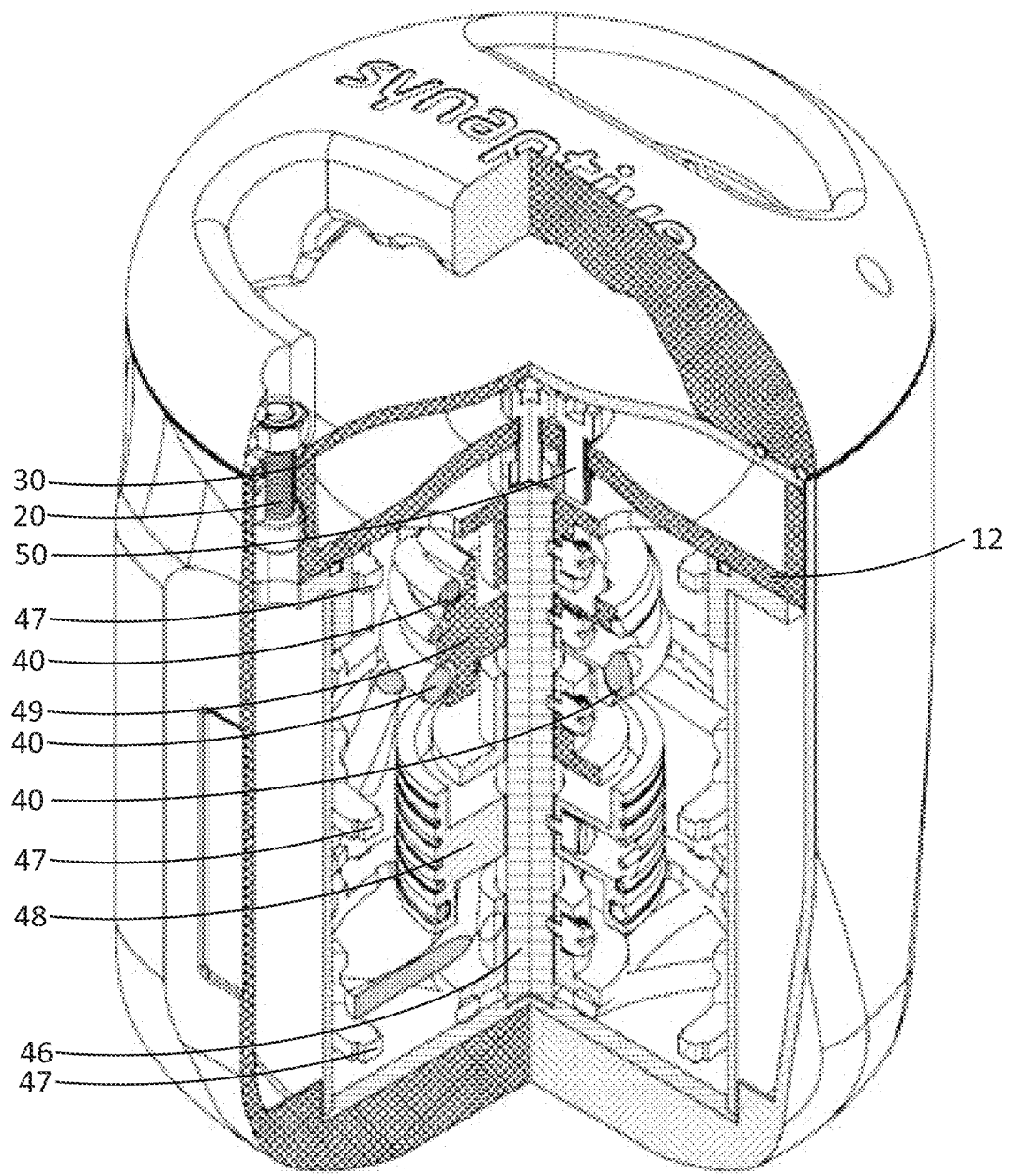
FIG. 4 is a cut out view of the elevation view of FIG. 1 showing the internal structure of the phantom.

In reference to the embodiment shown in FIG. 4, a central pillar 46 mounts to the base 12 and acts as support for the circular micro-rod bundle mounts 47, the resolution module 48 and the q-ball module 49. A micro-rod bundle 40 are shown associated with the circular bundle mounts 47. A plug 50 is used to seal the seal plate 30 after topping up matrix fluid during assembly.

The circular bundle mounts 47 act as a configurable support structure to the micro-rod bundles 40 and serve an additional purpose as fluid buffers to prevent fluid motion during a scanning protocol should the matrix material be fluid. This feature is to improve image clarity.

FIG. 6 is an extended exploded view of all components of the phantom of FIGS. 1 to 4. Micro-rod bundles 40 can be seen in FIGS. 5 and 6 where they are mounted in various orientations.

Referring to FIG. 5, once base 12 and internal housing 32 are sealed together, they are locked together using five (5) bolts 20 which are passed through holes in base 12 and corresponding holes in the peripheral shoulder in internal housing 32, indicated by the dashed lines and the bolts are threaded into their corresponding nuts as shown.

The flat bottom section of base 18 (i.e., exterior end) allows it to be securely placed on a bench-top or other flat surface. The handle provided by 34 in this section provides a grip for when a user is placing it into (and removing it from) an MRI head-coil. In addition, the flat surfaces 51 on the upper housing section 18 allows the user to steady the phantom 10 before transporting.

It should be noted that in some embodiments the phantom 10 is produced from a material capable of withstanding a freeze-thaw cycle if using a cryogel as matrix material. In addition the phantom 10 may include a marker (not shown) for landmarking and/or correct orientation in the MR coil.

In an alternate embodiment, the housing may be constructed and function as follows. Using various ties, the fiber modules are attached at their ends and along their lengths to three circular elements that are designed to enable the maximum number of fastening locations. These circular elements are attached to a center column that is mounted to an inner housing and they can slide, and be fastened to various locations on the column. These elements are unique in that they enable multiple configurations for fiber bundles to be positioned in x,y,z directions, 'kissing', diagonally, curved and interweaving. This center column also enables attachment of modules for various modules described in further detail below.

Description of Micro-Rods

Water can diffuse a radial distance of approximately 6-10 μm between the time of excitation and signal acquisition for a standard DTI protocol. This means that water within this distance from a micro-lumen channel wall or micro-rod wall will demonstrate restricted diffusion. Water that is not within this distance of a wall or barrier, will maintain free diffusion.

To increase the level of anisotropic diffusion within a micro-rod channel or against a micro-rod, it is useful to restrict the diffusion more in the radial direction. With increasing radial restriction (i.e. reduced radial dimension), this decreases water in the voxel which may decrease the received anisotropic signal. To promote ideal signal, the cross-sectional surface area needs to be increased to get more water within the voxel.

Two possible embodiments are disclosed in FIGS. 5 and 6, with respect to the fiber emulating micro-rod bundles 40 being mounted on the circular bundle mounts 47 in phantom 10 or in additional phantoms. In one embodiment, a flexible micro-lumen rod containing at least one (1) and as many as nineteen (19) micro-lumen channels of a diameter that allows an extreme aspect ratio may be used which facilitates the detection of diffusion in a liquid when the micro-lumen channels are filled with the liquid. The micro-lumen rod is comprised of a flexible material that allows it to be bent to span multiple directions and to isolate the liquid interior from the matrix material and it is cut to give desired lengths without cracking or otherwise deteriorating the inner structure. The micro-lumen channels can be filled by a number of methods including vacuum backfilling.

Figure 7:
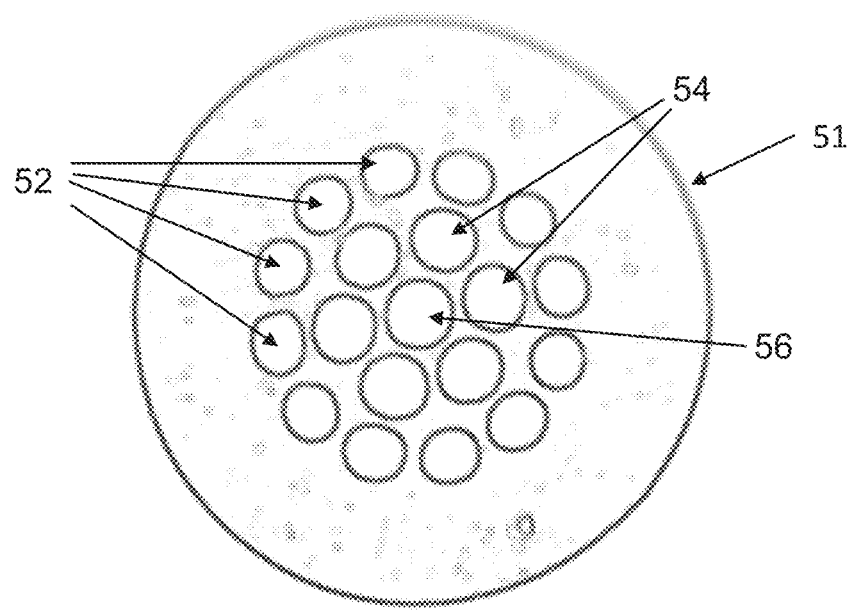
FIG. 7 is a cross sectional view of a nineteen (19) hole micro-rod which may form part of the present phantom having different sizes of hole diameters.
Figure 8:
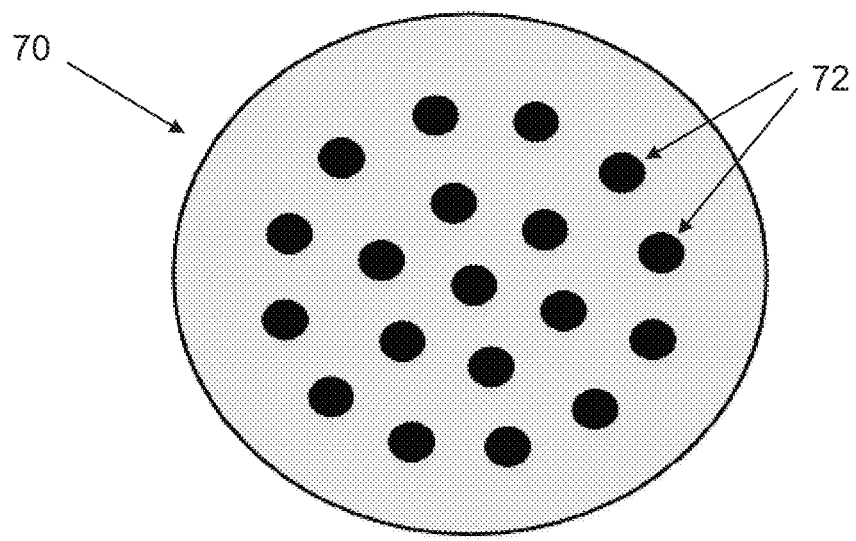
FIG. 8 is a cross sectional view of a nineteen (19) hole micro-rod which may form part of the present phantom having one size of hole diameters.

FIG. 7 shows a cross sectional view of one such embodiment of a flexible micro-rods 52, 54 and 56 having nineteen (19) channels of three different sizes. A single central channel 56 has the largest diameter, six (6) channels 54 of a slightly smaller diameter surround the central micro-lumen channel 56, and twelve (12) smaller diameter channels 52 surround channels 54. FIG. 8 shows a cross sectional view of another embodiment of a flexble micro-rod 70 which also contains nineteen (19) micro-channels 72 all having the same diameter.

The micro-rod embodiments in FIGS. 7 and 8 are non-limiting example embodiments of flexible micro-rods with multiple micro-lumen channels. It may be conceived that other micro-rod permutations with any number of micro-lumen channels and/or diameter sizes may be used. As an example, the micro-lumen channels as seen in FIGS. 7 and 8 may have a size in the range of 0.5 micrometers to 10 micrometers.

In an alternate approach, a flexible plastic micro-rod that is threaded with thread sizes proportional to the size of voxels may be used. This approach to axon fiber mimicry accounts for the fact that diffusion is restricted in the volume closest to the surface. The shapes disclosed herein are designed to balance the trade-off between increasing signal and restricting radial diffusion.

Figure 9:
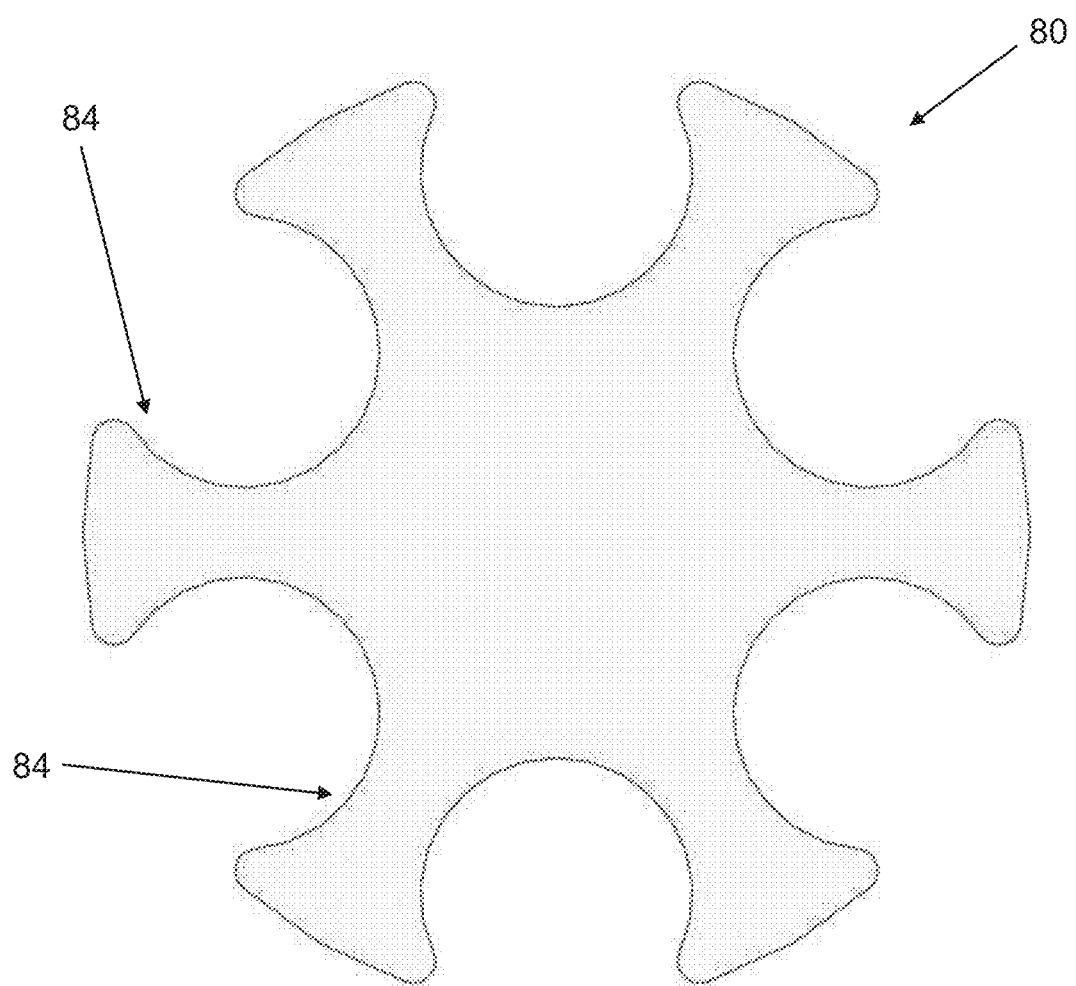
FIG. 9 is a cross sectional view of an embodiment of a flexible micro used to mimic cerebrospinal diffusion fiber tracts in the present diffusion phantom.

FIGS. 9 to 13 illustrates the cross-sectional views of several non-limiting embodiments of flexible pulled micro-rods used to mimic cerebrospinal diffusion fiber tracts in a diffusion phantom. The cross-section can be consistent along the entire length of the micro-rod and should be designed to maximize the wettable surface area of the micro-rod. For example, in the micro-rod structure 80. In FIG. 9, indentations with circular cross-sections 84 would maximize the wettable surface area.

Figure 10:
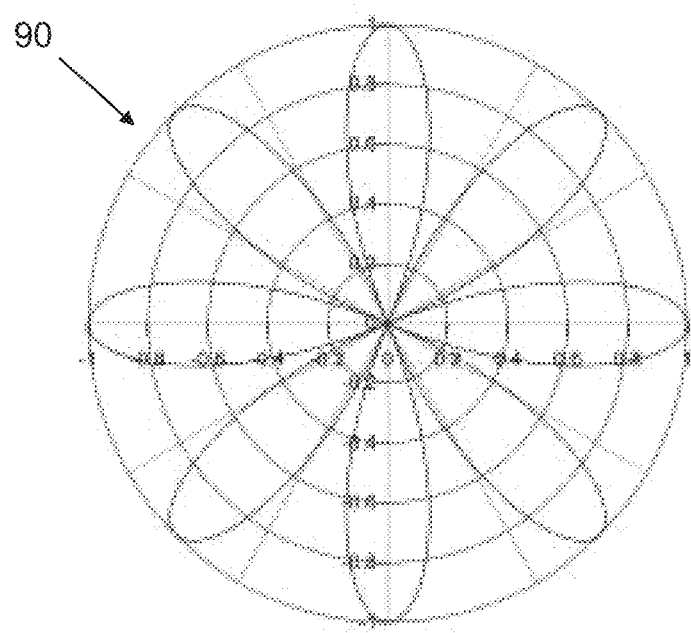
FIG. 10 is a cross sectional view of an alternate embodiment of a flexible micro-rod used to mimic cerebrospinal diffusion fiber tracts in the present diffusion phantom.

FIGS. 10 to 13 illustrates cross sections of alternate embodiments of pulled micro-rods forming part of the present disclosure. FIG. 10 is a cross sectional view of an alternate embodiment of a flexible micro-rod used to mimic cerebrospinal diffusion fiber tracts in the present diffusion phantom. In this embodiment in FIG. 10, a shape such as a rhodonea curve (where k=4) is representative of an idealized cross section where the surface area is maximized in each voxel. In a further embodiment, a fractal pattern (not shown) can also be used to maximize the wettable surface area and result in greater diffusion restriction in each voxel.

Figure 11:
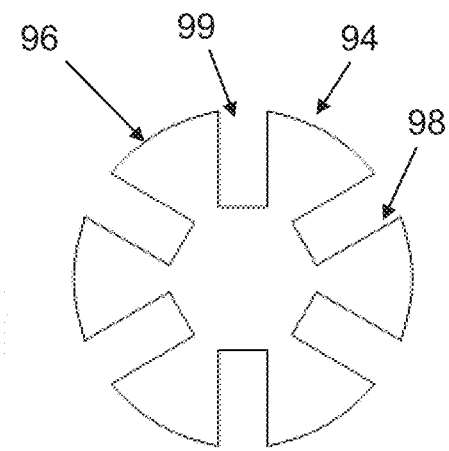
FIG. 11 shows a cross section of an embodiment of a pulled micro rod forming part of the present disclosure.
Figure 12:
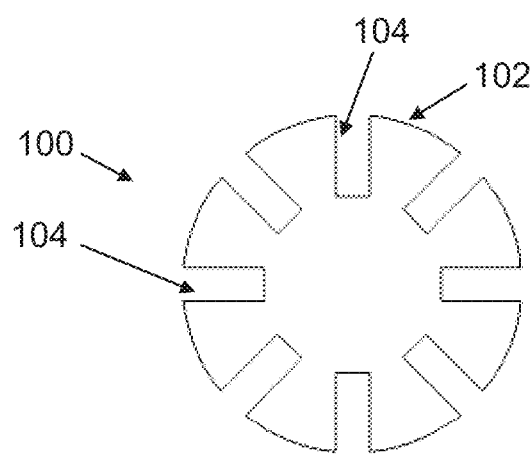
FIG. 12 shows a cross section of an alternate embodiment of a pulled micro-rod forming part of the present disclosure.

Referring to FIG. 11, micro-rod 94 includes a flexible pulled micro-rod material 96 showing six (6) indents or channels along the length of micro-rod 94. The embodiment of a micro-rod 100 in FIG. 12 shows a flexible pulled micro-rod material 102 having eight (8) indents or channels 104 running along the length of the rod 100. In a further embodiment shown in FIG. 13 at micro-rod 100, a pulled flexible micro-rod material 112 is shown having eight (8) channels 114.

Figure 13:
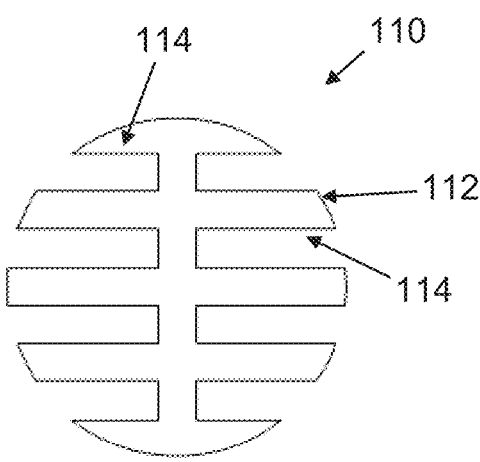
FIG. 13 shows a cross section of yet another alternate embodiment of a pulled micro-rod forming part of the present disclosure.

The indents or channels in the micro-rod surface seen in FIGS. 11 to 13 are chosen to be of a size to be narrow in comparison to the distance water can diffuse on the timescale of a DTI protocol, thereby restricting the possible diffusion in all directions except for along the direction of the fiber. It will be appreciated that the embodiments of FIGS. 9 to 13 are only exemplary in nature.

Description of Bicomponent Micro-Rods

Figure 14:
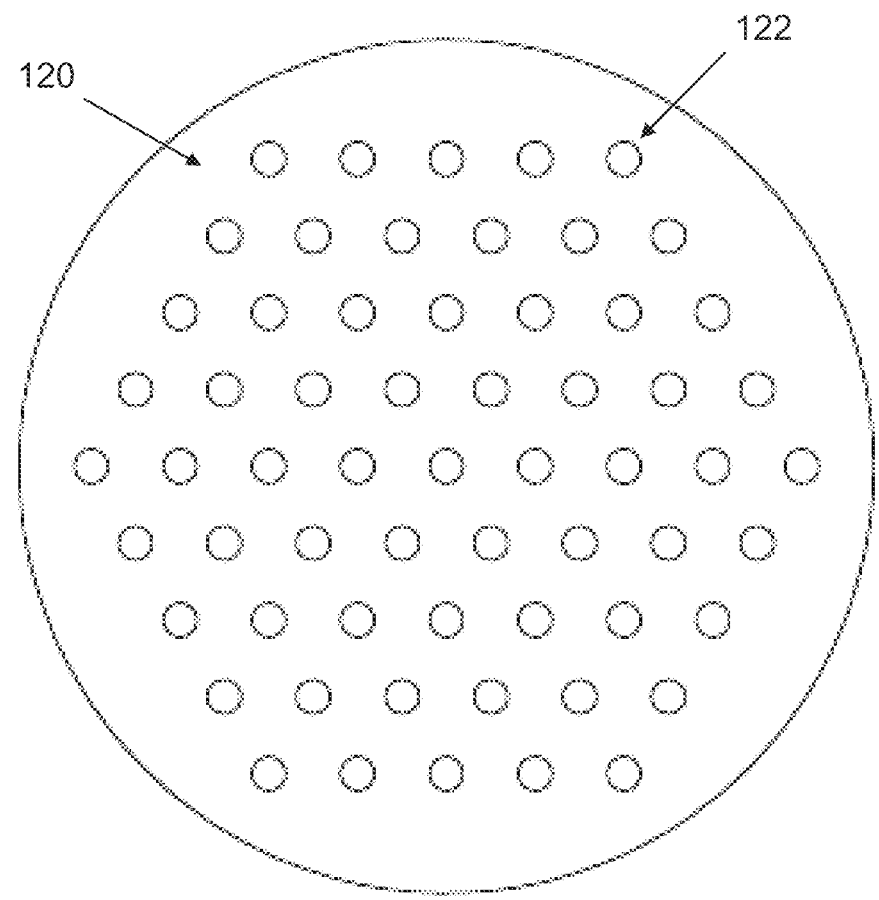
FIG. 14 shows the bi-material flexible micro-rod (Material B within Material A) before processing.

The embodiment shown in FIG. 14 incorporates the use of multi-rod bundles wherein the multi-rod bundles contain a multitude of bicomponent rods before the separation process (i.e, pre-processing stage). At this stage, there are a multitude of rods of Material B 122 embedded in Material A 120. These bicomponent rods may be extruded from the same spinneret (small, thimble-shaped, metal nozzle having fine holes through which a spinning solution is forced to form a micro-rod), resulting in both polymers contained within the same micro-rod.

FIG. 14 further depicts the cross-section of a bicomponent rod. In this embodiment, there are 61 micro-rods of Material B 122 made out of polypropylene (PP) that is surrounded by a water-soluble material Material A 120. Material A 120 in this embodiment may be polyvinyl alcohol (PVA). The micro-rods 122 made of Material B have substantially uniform diameter and are embedded through Material A 120 in substantially uniform spacing. Those skilled in the art would be able to determine appropriate substitutes for these materials. The 'sea' material can be removed by placing the fibers in warm water for a few hours, or using a combination of warm water and ultra-sonication as an example.

Figure 15:
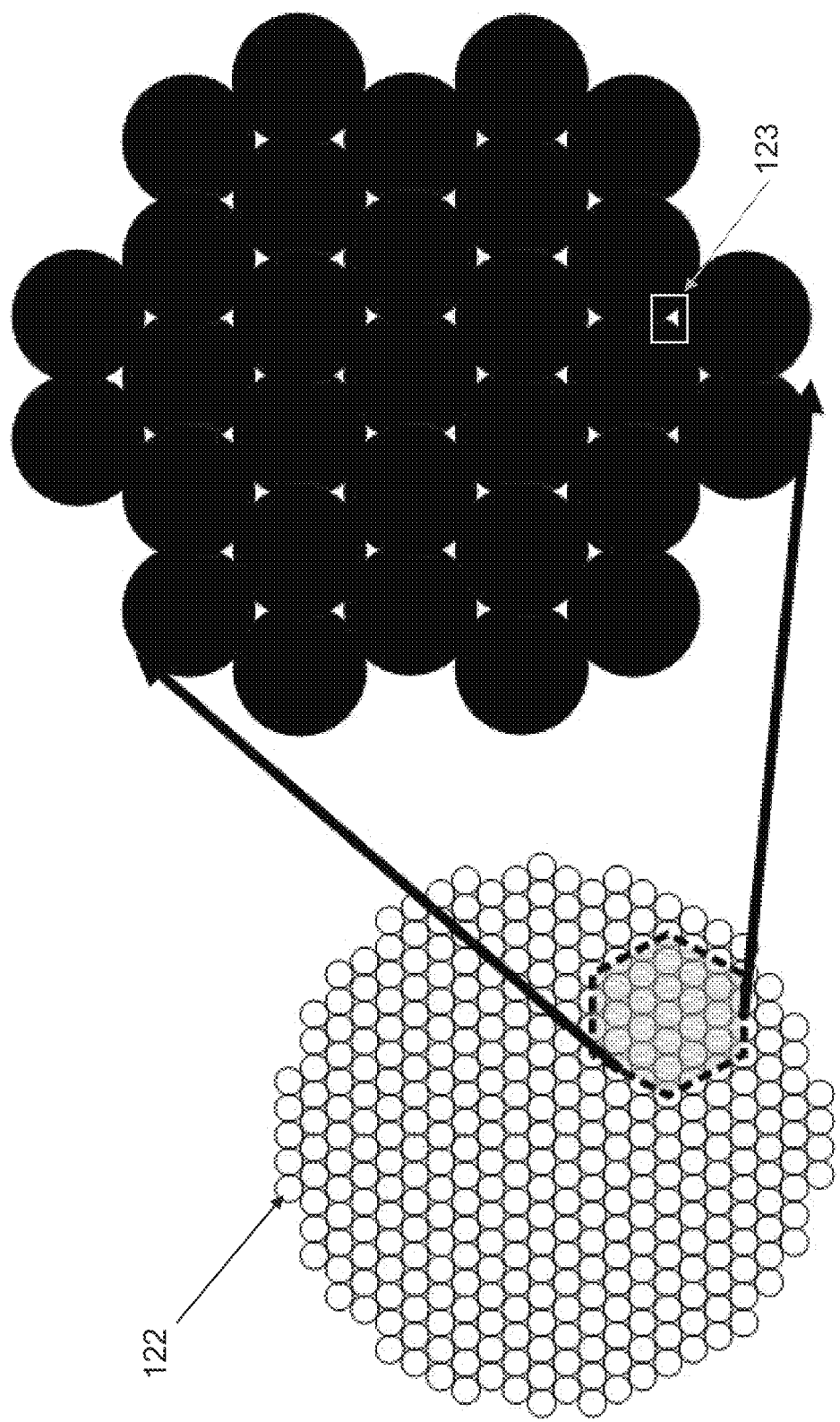
FIG. 15 shows the bi-material flexible micro-rod after processing (Material B only) with generated micro-lumen structure.

FIG. 15 shows the bi-material flexible micro-rod after removal of the Material A constituent, as well as, the unique micro-lumen regions generated by this process. It is these regions that function to provide anisotropic restriction of diffusion motion. The scale of the micro-lumen structure is dependent on the tightness of the packing of the micro-rod bundle, the diameter of the Material B micro-rods 122, and the sectional geometry of the rods themselves (i.e., they may contain the internal lumen structures as alluded to in FIGS. 7 to 13). Further, each micro-rod 122 of Material B is of substantially uniform spacing & uniform diameter based on manufacture tolerance requirements and/or limitations.

Description of Method of Forming Diffusion Fibers

Figure 16:
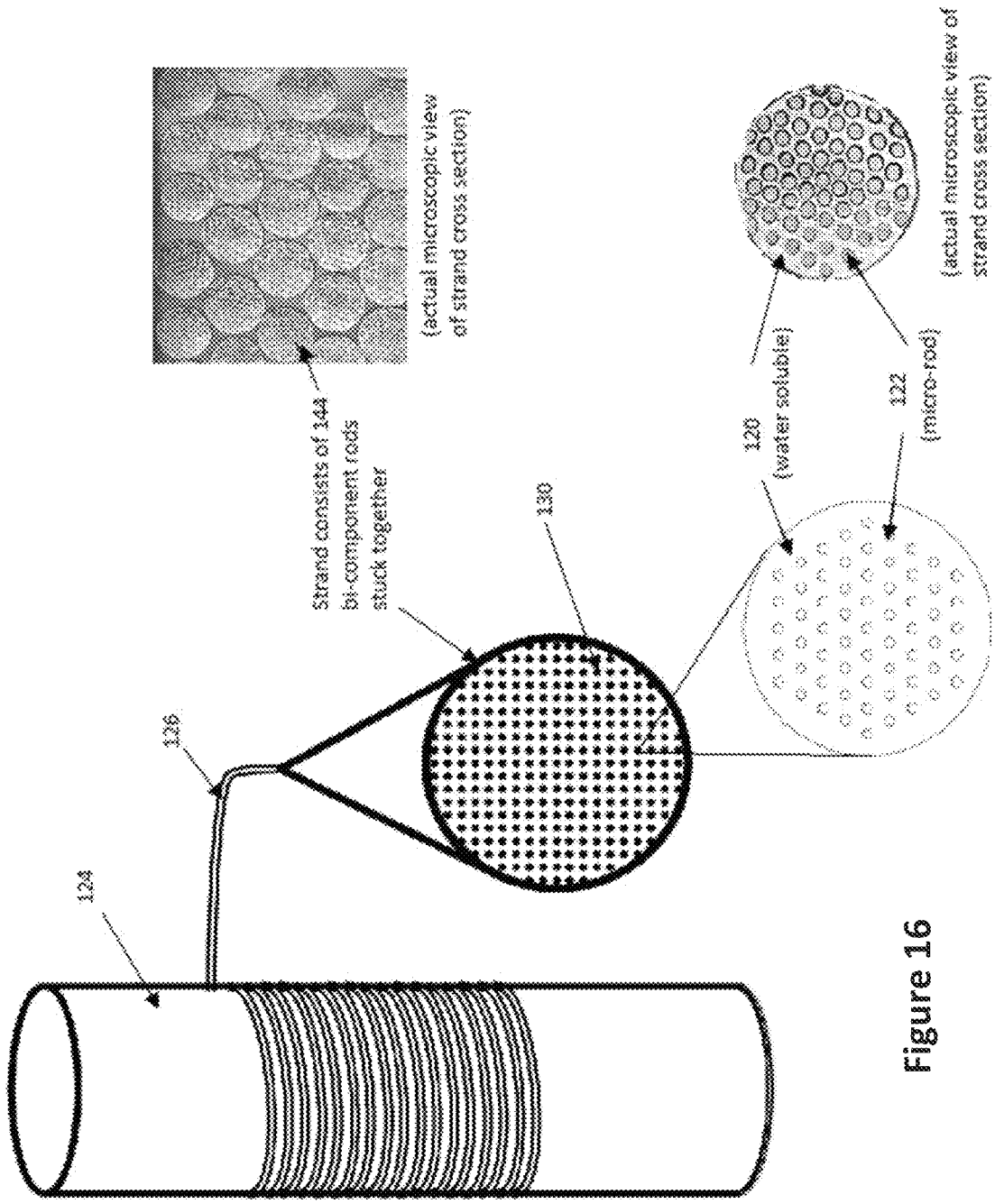
FIG. 16 shows the multi-material micro-rods before separation process.

FIG. 16 shows the bicomponent rods before the separation process. At this stage, there are a multitude of micro-rods 122 of material B (polypropylene (PP) embedded in the matrix 120 made of material A (polyvinyl alcohol (PVA)). FIG. 16 also illustrates bicomponent rod windings of fiber strands 126 on a production bobbin 124. In FIG. 16, the bicomponent rods 130 are wound on a bobbin 124 with 144 bicomponent rods per strand. Each strand 126 contains approximately 8800 polypropylene (PP) micro-rods (material B). The fiber strands 126 are wound onto a square shaped spindle 128 (see FIG. 17) using a motorized spinner to generate a rod bundle with a set number of aligned bicomponent rods 130. The revolutions are counted to determine the total number of micro-rods within the rod bundle. For example, 200 revolutions equates to 400 strands segments per bundle, resulting in a total of 3.5 million micro-rods per bundle.

To remove matrix 120 made of material A and introduce water between the micro-rods 122 (material B), the U-bolt containing the rod bundle is placed into a water bath for dissolving material A. Thereafter the material is then placed in an ultrasonication bath. The warm water and ultrasonication is then repeated one or more times to ensure complete removal of the PVA (material A).

In this embodiment, the strands 126 in FIG. 16 are initially brown in colour before removal of the PVA, and become white after the dissolving and ultrasonication process. Sonication also breaks up the micro-rods 122 (material B) and allows water to become entrapped between them.

The flexible micro-rod bundles 122 are then secured at each end to maintain alignment of the fibers using thread or zipties and are removed from the U-bolt. The flexible micro-rod bundles 122 can then be wrapped or manipulated to maintain a tight flexible micro-rod bundle and then fastened in various orientations to the interior of inner housing 32 suitable for MR imaging. In this example, the flexible micro-rod bundles 122 are tightly bundled using various techniques which may include, but are not limited to sewing thread, heat shrink tubing collars, ziptie collars, twisted fiber, or no manipulation. The zipties at the ends help keep tension on the flexible micro-rod bundles 122 to reduce motion during scanning.

Figure 17:
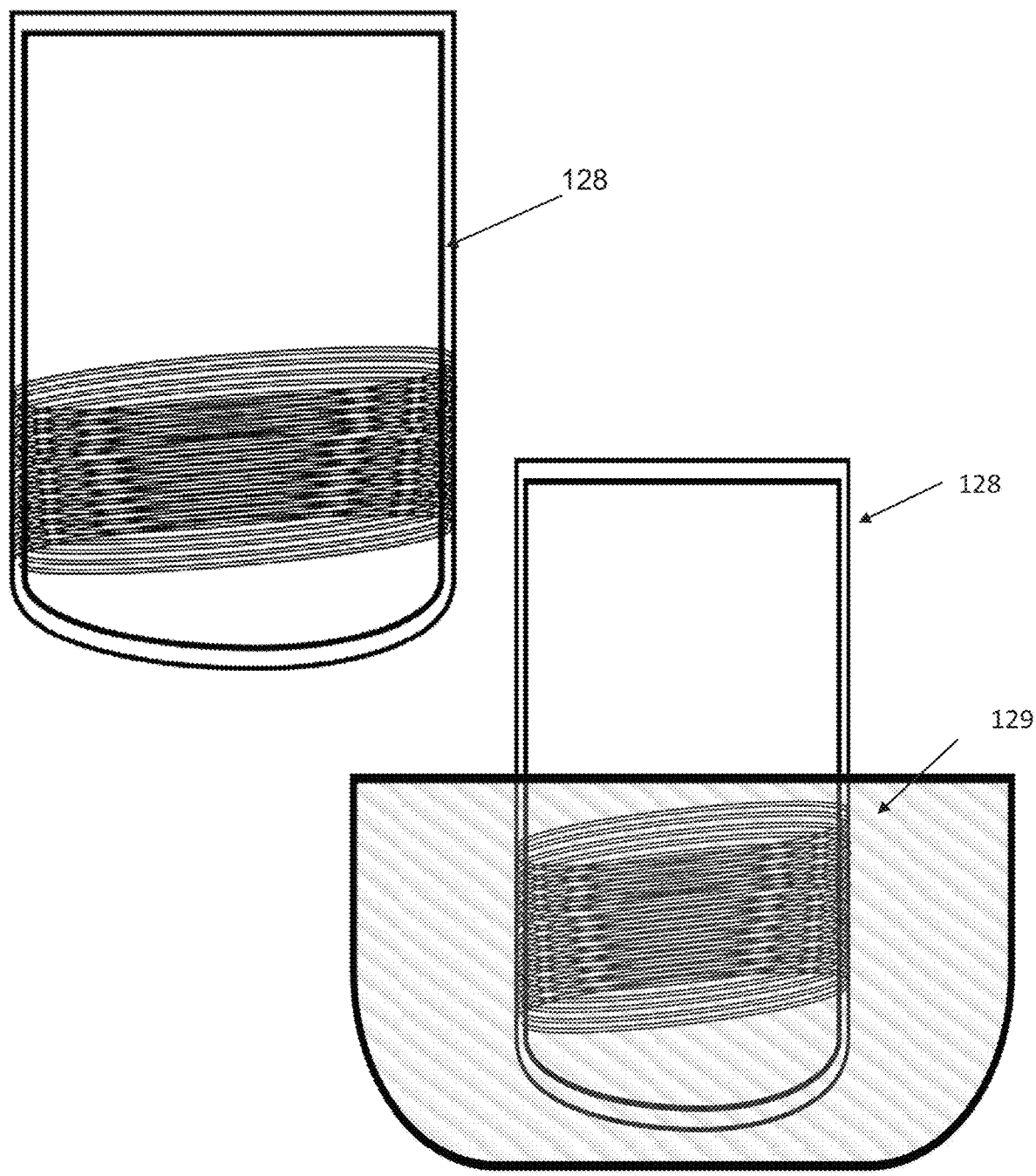
FIG. 17 illustrates how the strands are spun onto a spindle, heated and ultrasonicated in a water bath.

FIG. 17 illustrates how the strands are spun onto a spindle 128, heated and ultrasonicated in a water bath 129. In this embodiment, the spindle 128 is attached to a controlling motor which rotates the strands off of the bobbin 124 as seen in FIG. 16.

One advantage to using bicomponent micro-rod materials is that the alignment of the inner material 122 (material B) within a bicomponent rod 130 remains unaffected during the winding process and can only shift during the removal process of matrix 122 (material A). During this process, all micro-rods made of material B are under tension which should allow the material B to remain in an aligned configuration. This provides more uniform packing of the material B micro-rods 122 once the material A material is removed, in turn providing more uniform micro-lumen avenues between the material B micro-rods 122 where the anisotropic diffusion of water occurs.

Description of Micro-Rod Bundles Mounted on Module

Figure 18A:
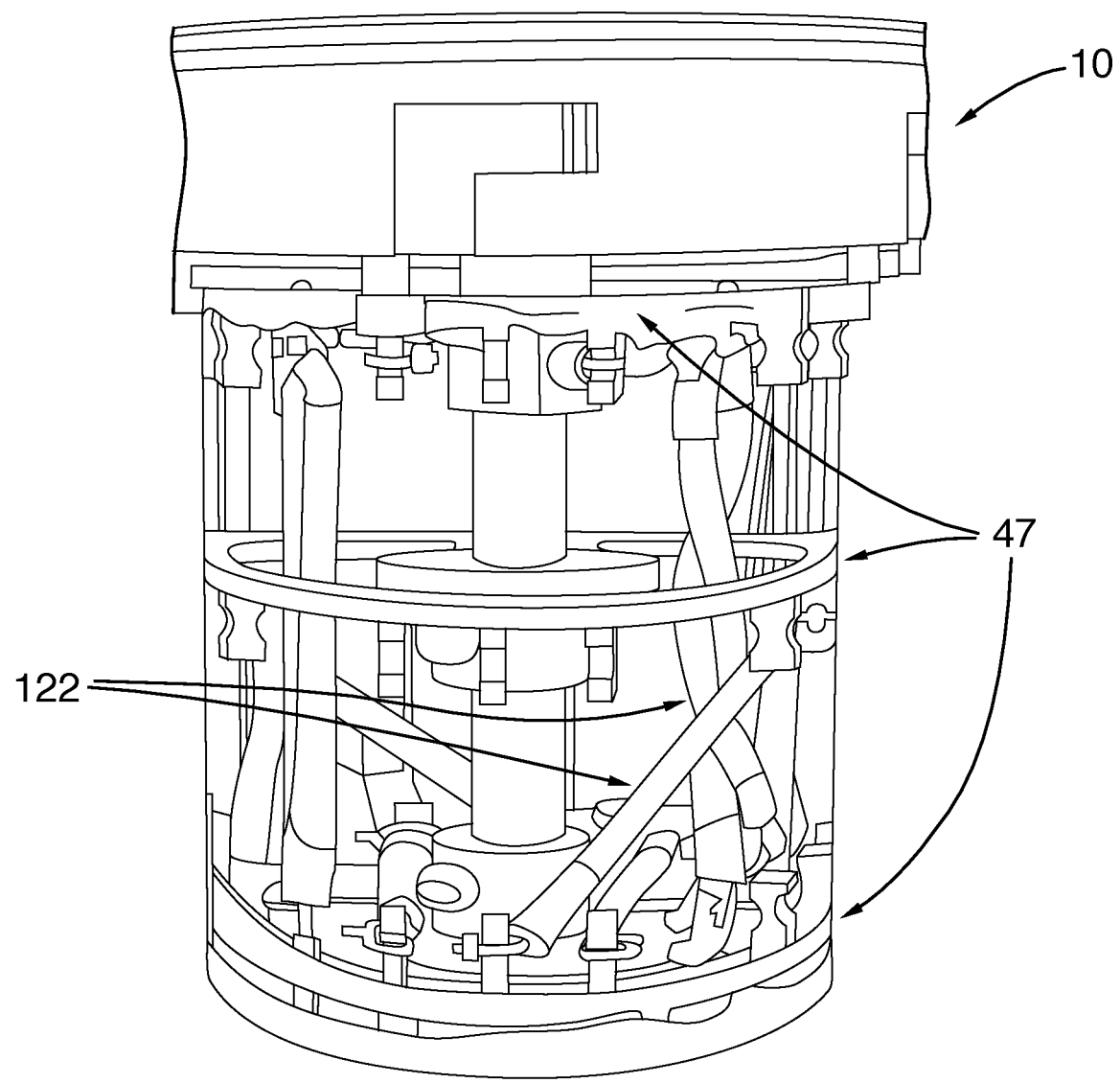
FIG. 18A illustrates the formed rod bundles fastened on the phantom.

FIG. 18A illustrates the formed micro-rod bundles, shown from the process illustrated in FIGS. 7 to 17. In FIG. 18A, the phantom is supported by the internal scaffold support structure also referred to as circular bundle mounts 47 so that the phantom simulates brain fibers travelling in all three orthogonal directions.

Using various ties, the micro-rod bundle modules are attached at their ends and along their lengths to three circular elements that are design to enable the maximum number of fastening locations. These circular elements are attached to a center column that is mounted to the main housing and they can slide, and be fastened to various locations on the column. These elements are unique in that they enable near infinite configurations for fiber bundles to be positioned in x,y,z directions, 'kissing', diagonally, curved and interweaving.

Figure 18B:
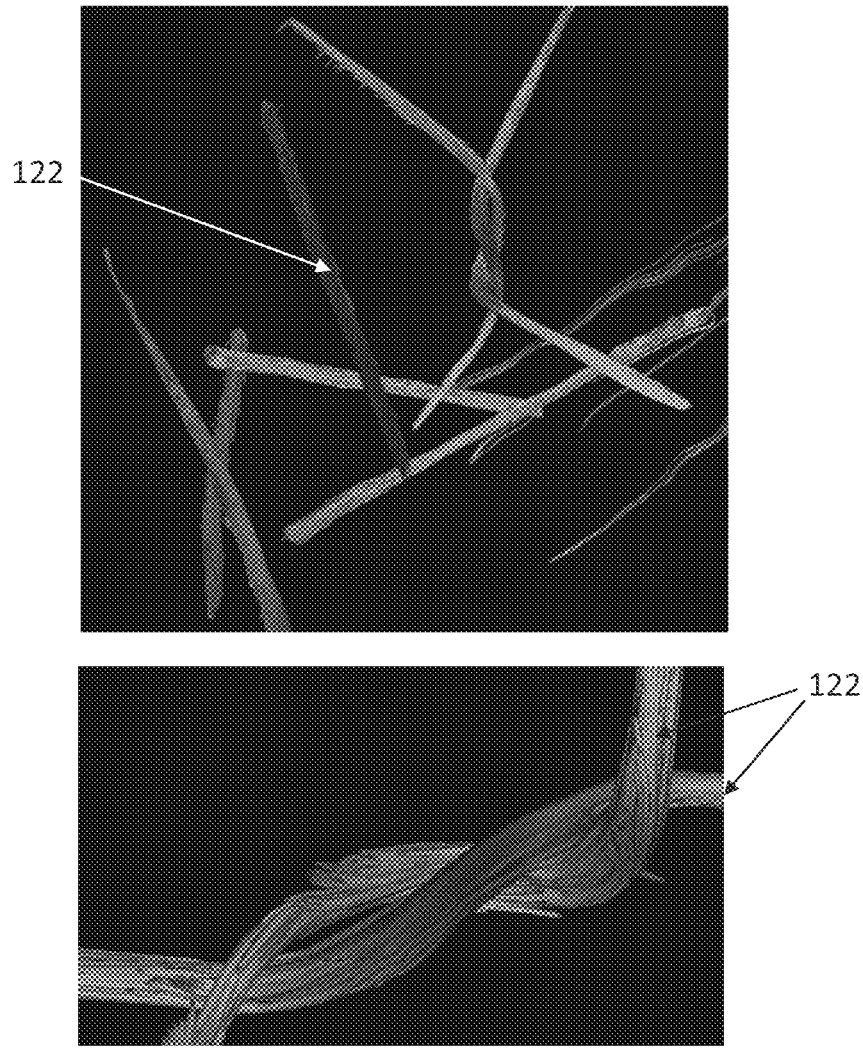
FIG. 18B illustrates a processed DTI image of micro-rod bundles supported within the phantom.

FIG. 18B illustrates a processed DTI image of micro-rod bundles supported within the phantom. The top image of FIG. 18B shows the DTI image of the micro-rod bundles. The bottom image of FIG. 18B provides a close-up magnified view of two strand of the micro-rod bundles.

FIGS. 18A and 18B are illustrative of a head phantom support structure for scanning the head region, however, the micro-rod bundles 122 and circular bundle mounts 47 may be incorporated into additional phantoms for scanning of other anatomical body parts (i.e., a diffusion phantom for a leg, spine, hip, abdominal regions, etc.) where anisotropic diffusion of water may be present in tissue and nerve images.

Tuning Matrix for T1 and T2 Values

As seen in FIG. 5, when assembled, internal housing 32 is sealed against base section 12 using o-ring 15, creating a liquid tight seal that encloses the matrix material. The micro-rod bundles 40 as shown in FIG. 18 are submerged in this matrix material.

Anisotropic diffusion is a function of the aspect ratio of the lumen micro-structure generated by the flexible micro-rod elements. By having an extreme length (i.e., infinitely long on the time scale of the MR acquisition) and a small width and height, this acts to restrict the direction that diffusion can take place to the direction of the micro-rod elements. Thus the liquid can be water or an aqueous based solution of a material to tune the MR visibility (e.g. copper sulfate solution).

To improve the MR visibility of the matrix material in the phantom, one can tune the MR properties of the matrix material to increase the relative signal within a typical MR diffusion measurement. The MR relaxation properties which control the relative amount of signal generated within an imaging sequence are the T1 and T2 relaxation times. The T1 relaxation rate determines how quickly the MR signal recovers in between repeated data acquisitions, thus to maximize signal in a DTI acquisition the T1 relaxation time should be short compared to the MR imaging repetition rate (TR). Similarly the T2 relaxation rate determines how quickly the MR signal decays away when trying to measure it so the T2 relaxation rate should be long relative to the time before data is acquired (commonly referred to as the time of echo, TE). As the liquid in the micro-lumen structure is aqueous, one can add soluble materials such as copper, nickel, and/or iron salts to change and optimize the T1 and T2 responses.

Description of Matrix Material

The diffusion phantom 10 disclosed herein may be filed with a matrix material which is chosen to be magnetic resonance (MR) compatible and give MR signals including signals in the range of human tissue. These materials could include but are not limited to polyvinyl alcohol (PVA) cryogel, PVA solution, cross-linked polyacrylate polymer gel, water, mineral oil or a solution of salt such as copper sulfate or similar materials. Exemplary formulations are disclosed in international publication WO/2015/003271, which is incorporated herein by reference in its entirety.

The matrix material is also interchangeable as the micro-rod bundles are modular and separable from the matrix. In other words the matrix material may be removed leaving the micro-rod bundles intact in its preselected configuration and replaced with a different matrix material if Description of Use Diffusion Phantom Utility One use for diffusion phantoms disclosed herein is for calibration and support of diffusion weighted magnetic resonance imaging (DW-MRI). A gold standard for the quantitative validation of DW-MRI is crucial for clinical purposes but is still not available. For the determination of the accuracy and precision and the evaluation of artifacts in a DW-MRI experiment, a phantom is required which has a well-known structure and diffusion behaviour similar to that in brain white matter. The use of phantoms with a well-known connectivity and anisotropy would also be useful for testing fiber tracking algorithms. Moreover, the origin of the DW-MRI signal in brain white matter is not completely understood. Several models exist, based on specific assumptions about the diffusion in the complex geometry of brain white matter. Validation of those models is also necessary.

Advantages of Micro-Rod Use for Lumen Generation

The diffusion phantom disclosed herein has several advantageous features. It can be configured to produce a diffusion signal along tracts in well-defined paths. The diffusion is produced using flexible micro-rods to generate multiple lumen microstructures, filled with water, or other useful liquids such as aqueous solutions containing contrast agents or salts that can help minimize magnetic susceptibility differences between fluid and micro-rods. These micro-rods can include preexisting lumen structures in their aspect ratio to increase the number of lumen within the flexible micro-rod bundle, as shown in FIGS. 7 to 13. This increases the diffusion signal since in this manner a greater volume of water will experience restricted diffusion at the lumen walls. It is noted that several separate lumen side by side are more effective than one large lumen, depending on the size. For example, if one large lumen is small enough that it will restrict the radial diffusion to the point of measurement then this is advantageous (if the wall is thin enough). It is preferred to maximize the amount of water in the voxel while also restricting diffusion so that there is enough non-water micro-lumen tube material to adequately restrict the diffusion.

As an alternative to using micro-rods with enclosed lumen, diffusion can be created with micro-rods with sectional profiles that are optimized to increase the perimeter area (i.e., outer surface). The diffusion signal can be increased in a scalable and predictable way by increasing the number of micro-rods passing through the same voxel. In this embodiment, it is preferable to increase the number of lumen to the point where the restricted radial diffusion is such that it can be measured in the DTI protocol. Any further increase in number of lumen would be unfavourable since there will be less water per voxel. This limit in the number of lumen needed will change based on the b-value of the diffusion sequence. For higher b-values there would be required more lumen, and conversely, for lower b-values, less lumen. This is because the b-value determines what diffusion length the system is sensitive to A lower b-value typically refers to a larger diffusion lengths and a higher b-value typically refers to a shorter diffusion lengths.

Description of Micro-Rod Bundle Support Structures

As discussed above, the micro-rod bundles 40, 122 are placed in a scaffold support structure comprised of circular holders 47 that allows for predictable, repeatable and stable mechanical positioning of the micro-rod bundles. When mounted on this scaffold structure, the micro-rod orientations may be chosen to demonstrate the ability to distinguish diffusion in orthogonal directions, along diagonal paths and in curved paths that change direction. Thus, the micro-rod bundles 40, 122 may be configured to provide a curved path and a U-shaped path to give some non-limiting exemplary configurations.

In one embodiment, the micro-rod bundle positioning can be configured to provide simulation of tractography of brain white matter fiber tracts wherein the simulated brain fiber tractography can display brain fiber tracts that touches, crosses or interweaves.

Thus, the set of micro-rod bundles described here is idealized simulation of nerve fibers, in that all orthogonal directions and curved paths are covered. In this embodiment, simulated nerve fibers that cross each other in the same voxel can be distinguished, and simulated nerve fibers that run together and then separate, can also be distinguished.

Description of Overall System

Figure 21:
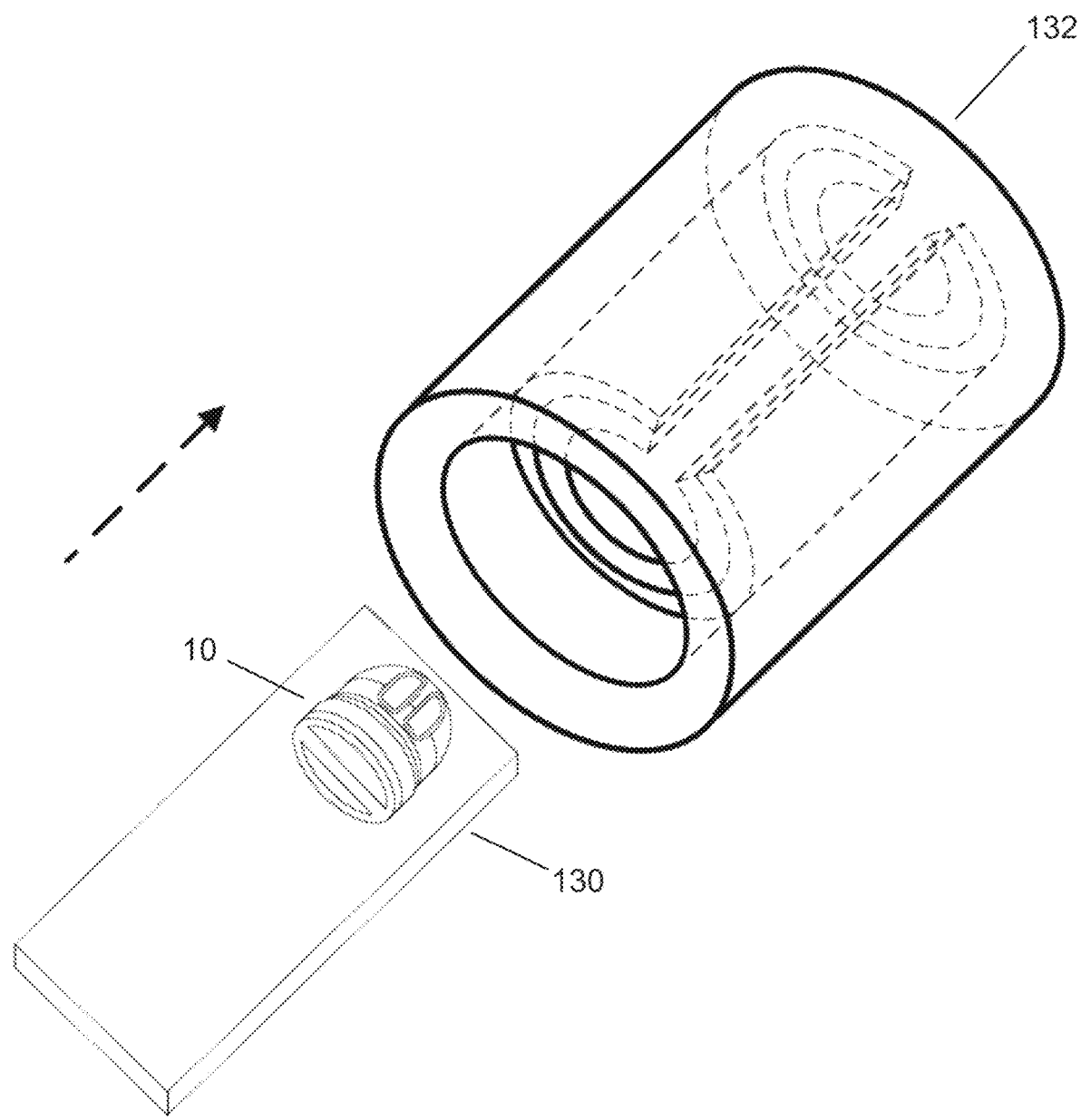
FIG. 21 is a perspective view showing a diffusion phantom constructed in accordance with the present invention being inserted into an MRI machine.

FIG. 21 is a perspective view showing a diffusion phantom 10 resting on a table 130 being inserted into an MRI device 132. The phantom 10 is placed on a flat surface 24 on table 130 as it is positioned inside the MRI machine.

Figure 22:
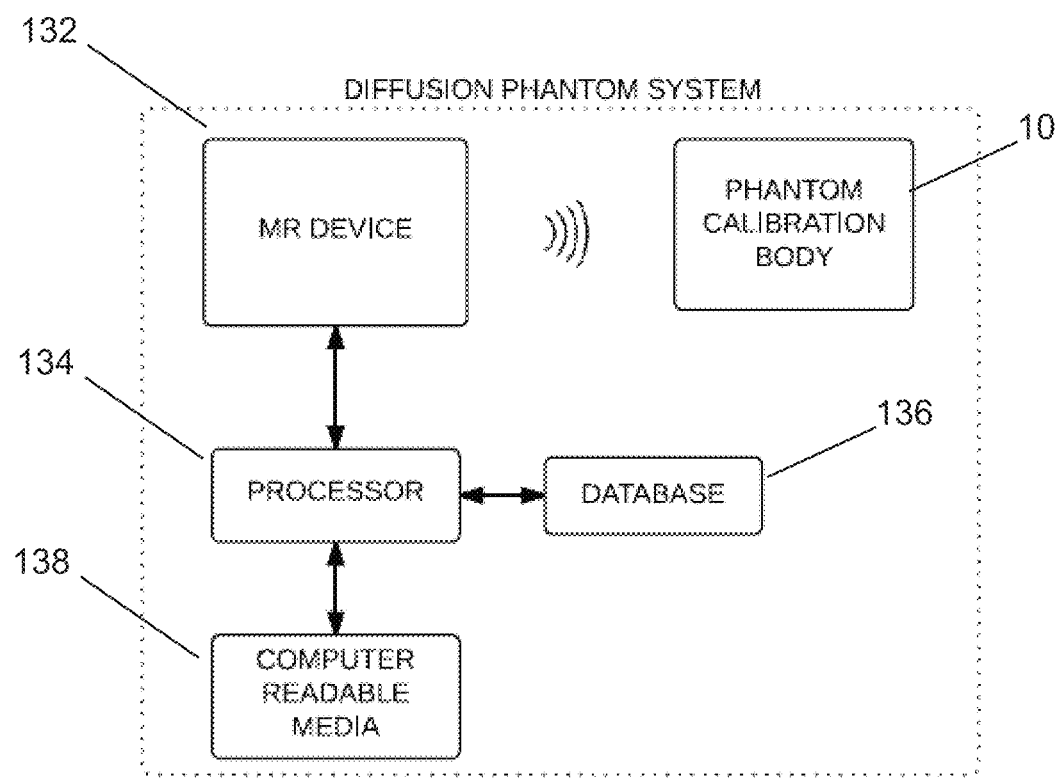
FIG. 22 high level diagram of a diffusion phantom system.

FIG. 22 high level system diffusion phantom system. The diffusion phantom 10 (or phantom calibration body) is placed onto into a MRI device 132, where the received signal can be acquired, processed and shared. The MRI device 132 may be connected to a computer processor 134, database 136 and computer readable media 138.

Description of Additional Modules

Partial volume effects (when a voxel contains two or more types of material) can be problematic in post-processing. By housing multiple micro-rod bundle thicknesses, an included resolution module 48, as seen in FIGS. 4 and 6, can be used to develop scanning methods that decrease resolution based biases. The resolution module 48 includes bicomponent rod bundles of varying diameters that can create DTI signals corresponding to the varying diameters. Resolution module 48 enables the MR technical to tune the MR machine protocols to obtain the desired DTI resolution.

In a further embodiment, the QBI (Q-ball imaging) module 49, as seen in FIGS. 4 and 6, can be used to validate more elaborate diffusion imaging techniques like Q-Ball Imaging by enabling the resolution of fiber crossings for evaluation of angular accuracy. The module is comprised of a column-mountable fixture which supports three intersecting and crossing rings of bicomponent rod bundles of different diameter. OBI module 49 is mounted to the center pillar 46 as seen in FIGS. 4 and 6. For supporting Q-Ball imaging, a sound measurement tool such as QBI module 49 is indispensable.

In a further embodiment (not shown), an isotropic diffusion module can be mounted to center pillar 46, similar to one seen in FIGS. 4 and 6. The isotropic module can enable calibration to a series of diffusion rates. The isotropic diffusion module is comprised of a column-mountable fixture which supports a multitude of vials containing a water-soluble polymer (i.e., povidone) in an aqueous solutions of various concentrations.

In an alternate embodiment, the phantom can accommodate a quality assurance module (QA module). One such example is the American College of Radiology (ACR) accreditation module. The QA module may be a separate module from the DTI module.

Figure 19A:
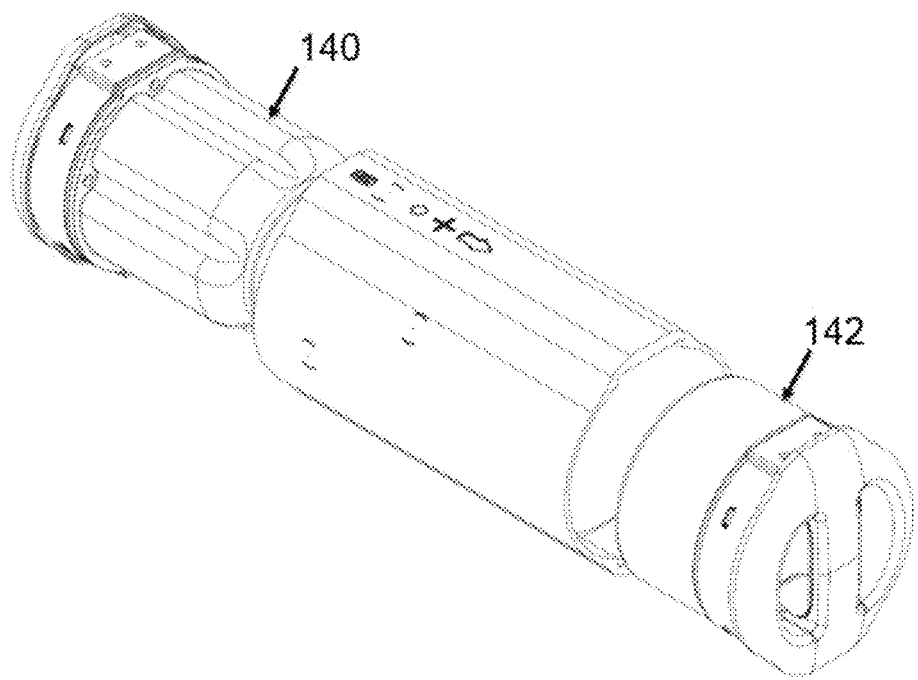
FIG. 19A shows and exploded view of the diffusion phantom.
Figure 19B:
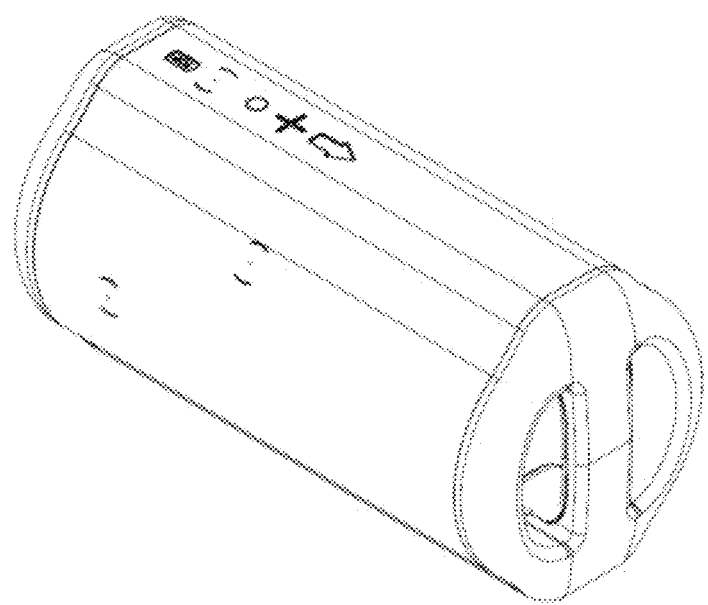
FIG. 19B shows an assembled view of diffusion phantom seen in FIG. 19A.

FIGS. 19A and 19B illustrates an exemplary diffusion phantom with a QA module and an anisotropic DTI module. FIG. 19A shows and exploded view of the diffusion phantom with both a DTI module 140 and QA module 142. FIG. 19B shows an assembled view of diffusion phantom seen in FIG. 19A.

The QA module 142, as seen in FIG. 19A includes necessary elements required for quality assurance verification and validation for ACR MRI accreditation. QA module 142 enables measurements of geometric accuracy, high-contrast spatial resolution, slice thickness accuracy, slice position accuracy, image intensity uniformity, percent-signal ghosting and low-contrast object detectability.

In further embodiments (not shown), the diffusion phantom as seen in FIGS. 19A and 19B may further comprise of a column-mountable plate. In an alternate embodiment, the center pillar 46 as seen in FIGS. 4 and 6 is secured at both ends by a vibration dampening element (not shown). A vibrational damping element will act to reduce vibration of the micro-rod bundle modules during the scanning process. This feature is to improve the image clarity.

In further alternate embodiments, microelectromechanical systems (MEMS) such as accelerometers and drop sensors can be attached to phantom 10 to monitor excess vibration. Further sensors such as thermometers can also be attached to phantom 10 to monitor temperature fluctuations.

Different bicomponent rods may be able to represent differentially myelinated nervous tissue by varying the spaces between the close packed structures of the difference radii of the micro-rod elements. This may be illustrated in FIG. 16 where by changing the relative spacing between micro-rod 122 within water-soluble Material A 120 would generate the DTI imaging characteristic of differentially myelinated nervous tissue. This gives us the ability to approximate the diffusion properties of a variety of structures.

A person skilled in the art using the aforementioned method of creating differentially myelinated nervous tissue would be able to create simulated version of different types (e.g. various types of tissues, such as tendons, ligaments, spinal cord, different fiber groups such as, corticospinal, SLF, IFO, corpus collosum; various nerve tissue models such as pediatric, natal, neonatal, in-utero; and different disease and injury states such as multiple sclerosis, edema, traumatic brain injury.

In a further embodiment, different processing conditions may be used to partially process the bicomponent rods to remove the water soluable matrix 120, (Material A) in FIG. 16, which could show partial diffusion and blocked channels along sections of the simulated axon fiber.

Figure 20:
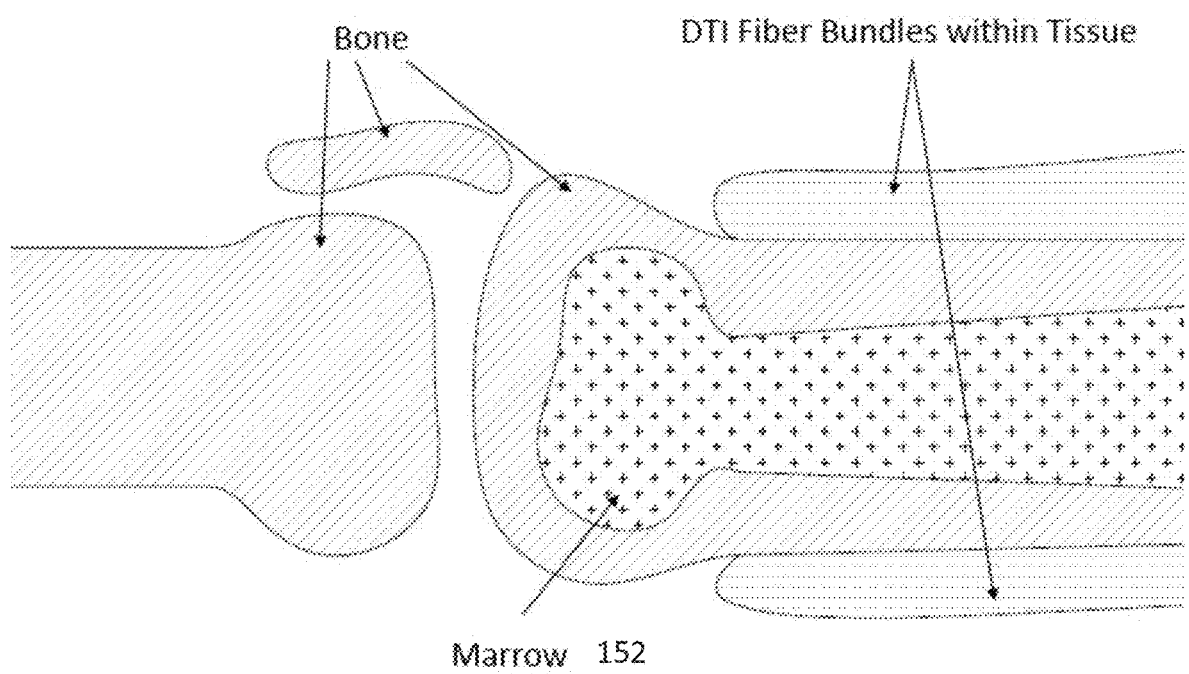
FIG. 20 illustrates an exemplary orthopedic phantom.

FIG. 20 illustrates an exemplary orthopedic phantom. The orthopedic phantom as seen in FIG. 20 may be used to mimic the structure of a knee, hip, spine or other orthopedic structures where it can be imaged in a MRI. One objective of the orthopedic phantom is to provide a calibration of these anatomical structures before an actual procedure.

The orthopedic phantom displays the diffusion tensor image (DTI) generation process and shows the flexibility of the micro-rod bundle manufacturing process to mimic diffusion signals corresponding to different tissues or different tissue states in the body.

The orthopedic phantom of FIG. 20, consist of a number of components to simulate bony structure, soft tissue, tendons and ligaments and fluids. The orthopedic phantom as seen in FIG. 20 illustrates a sectional view of a knee having bone structure 150, bone marrow 152 and simulated muscle tissue 154. Embedded within the simulated muscle tissue 154 are micro-rod bundles. In a further embodiment, the orthopedic phantom as seen in FIG. 20 may also include resolution and spatial modules to mimic staples or bone screws to test scanning abilities where an orthopedic implant is present.

While the applicant's teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without departing from the embodiments, the general scope of which is defined in the appended claims.

Except to the extent necessary or inherent in the processes themselves, no particular order to steps or stages of methods or processes described in this disclosure is intended or implied. In many cases the order of process steps may be varied without changing the purpose, effect, or import of the methods described.

The invention claimed is:

1. A cerebrospinal diffusion phantom, comprising:
   a) a housing having a shape and size configured for insertion into a magnetic resonance coil in one or more preselected poses;
   b) a plurality of elongated diffusion mimicking members contained within the housing, the plurality of elongated diffusion mimicking members positioned such that the elongated diffusion mimicking members extend in directions needed to substantially emulate a three-dimensional (3D) arrangement of cerebrospinal diffusion fiber tracts in a living organism, each elongated diffusion mimicking member including a liquid component which can undergo diffusion along the elongated diffusion mimicking member; and
   c) a cerebrospinal tissue mimic matrix material contained and sealed in the housing enveloping the plurality of elongated diffusion mimicking members, the housing being made of a material whose magnetic susceptibility substantially matches that of the cerebrospinal tissue mimic matrix material.

2. The phantom according to claim 1, wherein the elongated diffusion mimicking members are comprised of a flexible fiber.

3. The phantom according to claim 2, wherein the flexible fiber includes a micro-rod bundle having an assembly of micro-rods with uniform and varying cross-sectional planform so as to generate micro-lumen structures that are filled with liquid solution.

4. The phantom according to claim 2, wherein the flexible fiber includes a sheet of fibers organized in a fanned or planer arrangement.

5. The phantom according to claim 1, wherein the elongated diffusion mimicking members are flexible pulled micro-rods having two or more channels formed in an outer surface thereof and extending along a length of the micro-rods to give a surface area that is higher compared to the flexible pulled micro-rods not having the two or more channels.

6. The phantom according to claim 5, wherein the two or more channels having a size selected to be of a size to be narrow in comparison to the distance liquid can diffuse on the timescale of a diffusion tensor imaging (DTI) protocol, thereby restricting the possible diffusion in all directions except for along the direction of the fiber.

7. The phantom according to claim 6, wherein the two or more channels range in size from about 0.5 to about 10 micrometers.

8. The phantom according to claim 5, wherein the one or more elongated diffusion mimicking members is a plurality of said flexible pulled micro-rods bundled together to form flexible micro-rod bundles.

9. The phantom according to claim 1, wherein said cerebrospinal mimic matrix material is any one or combination of a polyvinyl alcohol cryogel (PVA-C), solution, water, or a cross-linked polymer gel.

10. The phantom according to claim 9, wherein each elongated diffusion mimicking member is comprised of a plurality of flexible micro-rod elements, and wherein said aqueous component is a thin layer of liquid enveloping said flexible micro-rod elements such that when said phantom is placed in a magnetic field in a magnetic resonance imaging (MRI) machine, diffusion of water molecules in said thin layer of liquid enveloping said flexible micro-rod elements takes place.

11. The phantom according to claim 1, wherein the liquid component includes water and a contrast agent selected to reduce magnetic susceptibility differences between the liquid component and a material of which the elongated diffusion mimicking members are made from.

12. The phantom according to claim 1, wherein the housing includes an inlet port for filling the housing.

13. The phantom according to claim 1, wherein the housing includes one or more planar sections for resting on a flat surface when inserted into a magnetic coil of an MRI machine, and wherein said one or more planar sections located on the housing is correlated with the 3D arrangement of cerebrospinal diffusion fiber tracts in the living organism.

14. The phantom according to claim 1, further comprising one or more markers or landmarks located on an exterior surface of the housing for landmarking a preselected orientation of the phantom in the MR coil.

15. The phantom according to claim 1, further comprising one or more temperature sensors on the housing to indicate external temperature.

16. The phantom according to claim 1, further comprising an internal chamber compartment for insertion of a temperature probe.

17. The phantom according to claim 1, wherein the housing has a size and shape reflective of a human head, and wherein the cerebrospinal tissue mimic matrix material is selected to mimic preselected biomechanical properties of a human brain.

18. The phantom according to claim 1, further comprising an additional module mounted within the housing, the additional module selected from a list consisting of:
   a resolution module configured to enable an MR technician to tune MR machine protocols to obtain a desired DTI resolution;
   a Q-ball imaging module for evaluation of angular accuracy of tractography in DTI;
   an isotropic diffusion module for calibration of multiple different isotropic diffusion rates;
   a quality assurance module configured for referencing phantom to images from known protocols; and/or a resolution module for determining high-contrast spatial resolution.

19. A method for generating biomimetic micro-lumen structure containing bundles of flexible micro-rods from multi-material elements, comprising:
  providing a bicomponent micro-rod bundle comprised of insoluble material embedded in a matrix of soluble material with a set number of aligned bicomponent micro-rod strands, the rod bundle having opposed ends;
  immersing the rod bundle in a solvent until all the soluble material has been removed and the solvent is entrapped between adjacent micro-rods of insoluble material;
  applying a stress to the rod bundle to align the micro-rods with each other in the bundle; and
  fastening the rod bundle on an interior of a cerebrospinal phantom to mimic diffusion tracts in cerebrospinal tissue.

20. The method of claim 19, wherein the bicomponent micro-rod represents differentially myelinated nervous tissue by varying the dimensions of the micro-rod elements used.

* * * * *